United States Patent [19]

Finbow et al.

[11] Patent Number: 5,668,302
[45] Date of Patent: Sep. 16, 1997

[54] ELECTROCHEMICAL GAS SENSOR ASSEMBLY

[75] Inventors: John Robert Finbow; Malcolm Robert Bulpitt, both of Hampshire, United Kingdom; Steven Allan Wylie Dejaray, 5750 Seaview Road, West Vancouver, British Columbia, Canada, V7W 1P8

[73] Assignees: City Technology Limited, Portsmouth, United Kingdom; Steven Allan Wylie Dejaray, Vancouver, Canada

[21] Appl. No.: 653,414

[22] Filed: May 24, 1996

[30] Foreign Application Priority Data

May 24, 1995 [GB] United Kingdom ............ 9510454

[51] Int. Cl.[6] .................................................. G01N 7/00
[52] U.S. Cl. ...................................... 73/23.2; 73/1.06
[58] Field of Search .................. 73/1 G, 23.2; 204/412

[56] References Cited

U.S. PATENT DOCUMENTS

| | | | |
|---|---|---|---|
| 3,787,308 | 1/1974 | Malaspina et al. | 204/195 P |
| 4,151,739 | 5/1979 | Breuer | 73/1 G |
| 4,207,159 | 6/1980 | Kimura | 204/195 S |
| 4,224,113 | 9/1980 | Kimura | 204/1 T |
| 4,399,017 | 8/1983 | Inoue et al. | 204/425 |
| 4,489,590 | 12/1984 | Hadden | 73/1 G |
| 4,742,708 | 5/1988 | Porter | 73/1 G |
| 4,828,671 | 5/1989 | Lin et al. | 204/412 |
| 4,828,672 | 5/1989 | Lin et al. | 204/424 |
| 4,900,422 | 2/1990 | Bryan et al. | 204/412 |
| 4,902,402 | 2/1990 | Pebler et al. | 204/427 |
| 4,927,517 | 5/1990 | Mizutani et al. | 204/412 |
| 5,098,545 | 3/1992 | Patko | 204/412 |
| 5,098,547 | 3/1992 | Bryan et al. | 204/412 |
| 5,215,644 | 6/1993 | Ashikaga | 204/412 |
| 5,273,640 | 12/1993 | Kusanagi et al. | 204/412 |

FOREIGN PATENT DOCUMENTS 0 611 112 8/1994 European Pat. Off. .
2 254 696 10/1992 United Kingdom .

*Primary Examiner*—Hezron E. Williams
*Assistant Examiner*—Jay L. Politzer
*Attorney, Agent, or Firm*—Lee, Mann, Smith, McWilliams, Sweeney & Ohlson

[57] ABSTRACT

An electrochemical gas sensor assembly comprises an electrochemical gas sensor (1) including sensing (39) and counter (32) electrodes, an intervening body of electrolyte contacting the electrodes, and means (5) for controlling the diffusion of gas to the sensing electrode. A test gas generator (7) is connected to the sensor so as to supply a test gas directly to the sensing electrode (39) by-passing the gas diffusion control means (5).

6 Claims, 2 Drawing Sheets

ELECTROCHEMICAL GAS SENSOR ASSEMBLY

FIELD OF THE INVENTION

The invention relates to an electrochemical gas sensor assembly including an electrochemical gas sensor having sensing and counter electrodes, an intervening body of electrolyte contacting the electrodes, and means for controlling the diffusion of gas to the sensing electrode such as a solid membrane, gas phase or Knudsen diffusion barrier.

DESCRIPTION OF THE PRIOR ART

Electrochemical gas sensors of this kind are well known and are used to sense a variety of gases including oxygen, and toxic gases such as hydrogen sulphide, carbon monoxide etc. Gas sensors have a limited lifetime and it is important to know whether or not the sensor is still active.

GB-A-2254696 illustrates a gas sensor device in which the gas sensor is provided within an enclosure provided with a gas-permeable opening in the form of a sintered stainless steel disc. This allows the sensor to detect inflammable gases by minimising the risk of the sensor causing an explosion. The sensor described is a MOS sensor but the document indicates that this could be substituted by an electrochemical sensor. A gas generator is provided within the enclosure to generate a gas for calibration purposes. The problem with this construction is that the gas generated by the calibration gas generator cannot give an immediate indication as to whether or not the sensor is alive or active due to the time required for the gas to reach the sensing electrode where, in the case of an electrochemical gas sensor, it will have to diffuse through a controlling diffusion barrier in order to reach the sensing electrode.

SUMMARY OF THE INVENTION

In accordance with the present invention, an electrochemical gas sensor assembly comprises an electrochemical gas sensor including sensing and counter electrodes, an intervening body of electrolyte contacting the electrodes, and means for controlling the diffusion of gas to the sensing electrode and is characterised in that a test gas generator is connected to the sensor so as to supply a test gas directly to the sensing electrode by-passing the gas diffusion control means.

We have devised a new sensor assembly which includes a test gas generator enabling the in situ generation of a test gas such as a "checking" or calibration gas which will cause a response in the sensor enabling the user to check that the sensor is alive. The test gas is introduced directly to the sensor without passing through the gas diffusion control means and thus achieves a rapid response.

The test gas generator can take a variety of forms but conveniently comprises an electrolyser. Other possibilities include the use of a chemical which, when heated (e.g. electrically) gives off a gas; and a source of pressurized gas linked to the sensor via an electrically controlled valve. The test gas generator is conveniently mounted to a member which includes the gas diffusion control means although in other applications the generator could be positioned remote from the sensor and linked to it by a gas conduit. Where the gas generator is mounted to the said member, preferably an outlet of the gas generator is positioned over an aperture in the member, the aperture in the member having a size sufficient to enable transport of gas therethrough, for example by diffusion or bulk flow.

Typically, the gas generator will have a gas outlet including a membrane through which the test gas can diffuse but which prevents passage of electrolyte.

The gas sensor can be of any conventional form and will typically also include a reference electrode while the test gas generator will be constructed according to the gas to which the sensor is sensitive. In particular, where the test gas generator is an electrolyser, the electrolyte and/or electrodes of the electrolyser will be chosen in accordance with the gas to be generated.

The means for controlling the diffusion of gas may comprise a gas phase diffusion barrier, a Knudsen diffusion barrier or a solid membrane.

BRIEF DESCRIPTION OF THE DRAWINGS

An example of an electrochemical gas sensor assembly according to the invention will now be described with reference to the accompanying drawings, in which.

DETAILED DESCRIPTION OF EMBODIMENT

Figure 4:
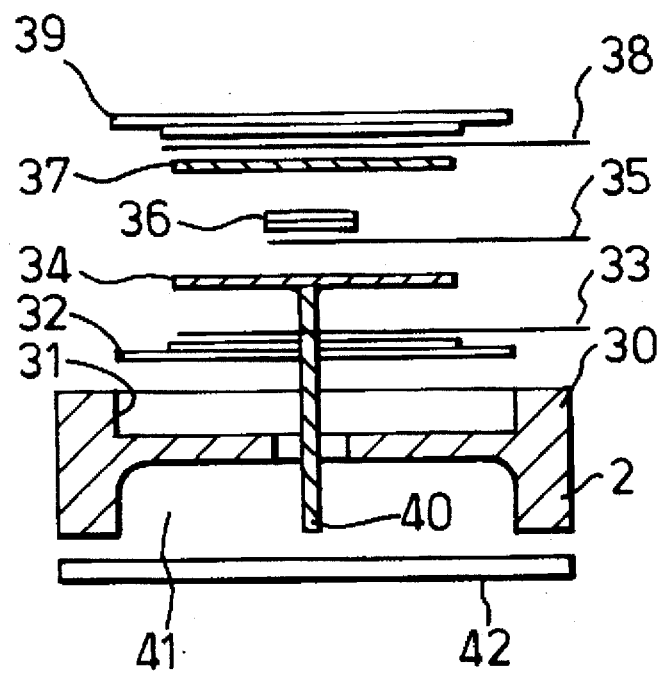
FIG. 4 is an exploded view of the electrochemical gas sensor shown in FIG. 1.

The assembly shown in the drawings comprises an electrochemical gas sensor 1 of conventional form which is shown in more detail in FIG. 4. The sensor 1 includes a base 2 having an outwardly facing, annular flange 30 defining an electrode well 31. Within the electrode well 31 are provided a counter electrode 32 comprising PTFE tape and a catalyst layer connected to a current collector 33. The counter electrode 32 is provided in a sandwich with a separator 34, a further current collector 35, a reference electrode 36 (comprising PTFE layer and catalyst), a separator 37, a current collector 38, and a sensing electrode 39 (again of PTFE and catalyst). A wick 40 extends from the separator 34 through the apertures in the counter electrode 32 and base 2 into an electrolyte reservoir 41 containing the electrolyte. The reservoir 41 is sealed by an end plate/seal 42.

The base 2 is mounted to a sensor top plate 3 with an intervening "O" ring 4. The sensor top plate 3 includes a capillary 5 defining a gas phase diffusion barrier through which gas to be detected diffuses.

Figure 1:
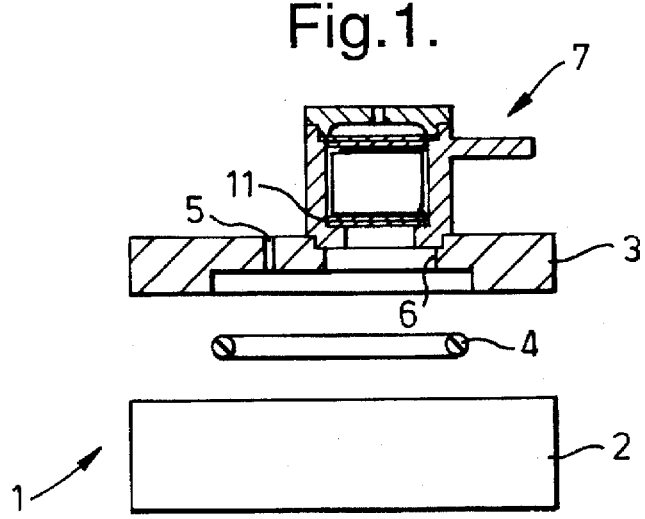
FIG. 1 is a partially exploded, part sectional view of the assembly.
Figure 2:
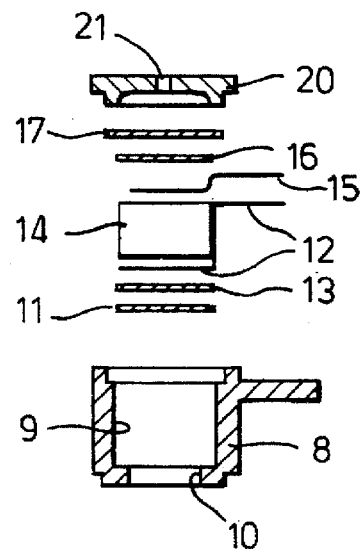
FIG. 2 is an exploded section through the electrolyser shown in FIG. 1.
Figure 3:
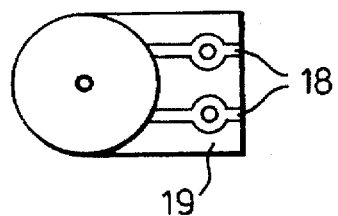
FIG. 3 is a plan of the electrolyser.

The components described so far are conventional except that the sensor top plate 3 has an additional aperture 6 (through which transport of gas can occur) to which an electrolyser 7 is mounted. The electrolyser is shown in more detail in FIGS. 2 and 3.

The electrolyser includes a base 8 defining a chamber 9 having an outlet aperture 10. A PTFE membrane 11 is heat sealed to the bottom of the chamber 9. An electrode 12 of for example platinum foil extends above the membrane 11 and is optionally separated from the membrane by a separator 13.

Above the electrode 12 is positioned a porous structure 14 of for example VYON containing electrolyte such as aqueous sulphuric acid depending upon the test gas to be generated. Alternative electrolytes are a gelled electrolyte, or liquid electrolyte.

A second, counter electrode 15 is positioned above the member 14 and an optional separator 16 is located between the electrode 15 and a further member of for example PTFE 17 which seals the top of the electrolyser chamber 9. The electrodes 12,15 are taken to external contacts 18 on a connector lug 19.

A top cap 20 closes the chamber 9 and assists sealing of the membrane 17 and electrodes 12,15. A vent 21 is provided in the top cap 20.

When it is wished to check that the sensor 1 is operational, a potential is applied across the electrodes 12,15 to drive a current which causes electrolysis of the electrolyte formed by or contained in the member 14. The current polarity is such that hydrogen is evolved from the electrode 12 and oxygen from the electrode 15. Oxygen gas is vented from the chamber 9 through the membrane 17 and out through the vent hole 21 while hydrogen gas diffuses through the membrane 11 and the opening 10 into the sensor 1 directly to the sensing electrode where it causes an electrochemical reaction and a resultant signal. In this example, the sensor 1 responds to hydrogen and thus comprises for example a carbon monoxide sensor.

By employing different materials at the electrode 12 other gases can be generated to check other types of sensor, for example $H_2S$ or HCN. Reference is made to EP-A-0611112. Alternatively, different electrolytes and/or electrodes can generate other gases, such as chlorine from chloride containing electrolytes.

In some cases, the vent hole 21 is omitted. This is possible in the case where the electrolyte is confined within a porous structure such as VYON. In that event a space can be formed around the VYON so that gas generated at the electrode 15 passes forward through the space and into the sensor 2 where it is vented.

With constructions according to the invention, very rapid response times can be achieved of the order of a few seconds, typically no more than 10 seconds, with recovery times in the order of seconds to a few minutes, typically no more than 5 minutes.

We claim:

1. An electrochemical gas sensor assembly comprising an electrochemical gas sensor including sensing and counter electrodes, an intervening body of electrolyte contacting said electrodes, and means for controlling the diffusion of gas to said sensing electrode, wherein a test gas generator is connected to said sensor so as to supply a test gas directly to said sensing electrode by-passing said gas diffusion control means.

2. An assembly according to claim 1, wherein said test gas generator comprises an electrolyser.

3. An assembly according to claim 1, wherein said test gas generator is mounted to said gas diffusion control means.

4. An assembly according to claim 3, wherein said test gas generator is mounted over an aperture defined in the said member, said aperture in said member having a size such that transport of gas through said aperture takes place.

5. An assembly according to claim 1, wherein said test gas generator includes a membrane through which test gas can diffuse but which prevents passage of electrolyte therethrough.

6. An assembly according to claim 1, wherein said gas diffusion control means of said sensor comprises one of a solid membrane, a gas phase diffusion barrier, or a Knudsen diffusion barrier.

* * * * *